(12) United States Patent
Holt et al.

(10) Patent No.: US 7,361,779 B1
(45) Date of Patent: Apr. 22, 2008

(54) LOW-MELTING MIXTURES OF DI-N-BUTYL AND DIISOBUTYL TEREPHTHALATE

(75) Inventors: Mark Holt, Huntersville, NC (US); Phillip Wayne Turner, Blountville, TN (US); Steven Leroy Cook, Kingsport, TN (US); Martin James Stimpson, Marlborough (GB)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 11/787,941

(22) Filed: Apr. 18, 2007

(51) Int. Cl.
*C07C 69/76* (2006.01)
*C07C 67/00* (2006.01)

(52) U.S. Cl. .......................................... 560/76; 560/96
(58) Field of Classification Search ..................... None
See application file for complete search history.

(56) References Cited

U.S. PATENT DOCUMENTS 4,675,434 A * 6/1987 Uhm et al. .................... 560/99

FOREIGN PATENT DOCUMENTS

| JP | 60004151 | 1/1985 |
|---|---|---|
| JP | 2005120019 | 5/2005 |
| JP | 2005306759 | 11/2005 |

* cited by examiner

*Primary Examiner*—Karl Puttlitz
(74) *Attorney, Agent, or Firm*—Bernard J. Graves, Jr.; Brett L Nelson (57) ABSTRACT

Mixtures of terephthalate diesters having lowered freezing points and methods of making the terephthalic acid diesters. The method includes contacting a first alcohol, a second different alcohol and dimethyl terephthalate in the presence of a catalyst to thereby form the terephthalate diesters.

10 Claims, 8 Drawing Sheets

DSC

LOW-MELTING MIXTURES OF DI-N-BUTYL AND DIISOBUTYL TEREPHTHALATE

FIELD OF THE INVENTION

This invention pertains to n-butyl isobutyl terephthalate and a mixture of terephthalic acid diesters having a low melting point. The invention also relates to the preparation of n-butyl isobutyl terephthalate and a mixture of terephthalic acid diesters.

BACKGROUND OF THE INVENTION

Terephthalic acid diesters, such as di-n-butyl terephthalate (DBT) and di-isobutyl terephthalate (DiBT), can be used as plasticizers in a variety of polymeric materials such as polyvinyl chloride. However, di-n-butyl terephthalate (DBT) has a melting point of about 16° C. Likewise, pure di-isobutyl terephthalate freezes at an even higher temperature of 54° C. This has led to the concern that these products could freeze when stored at cold temperatures. Freezing of such products often requires installation of heated tanks, transfer lines, and associated handling equipment, thus increasing the cost of using these products. The present invention addresses this concern by producing terephthalic acid diesters having a lowered melting point.

BRIEF SUMMARY OF THE INVENTION

A first embodiment of the present invention concerns a composition comprising n-butyl isobutyl terephthalate.

Another embodiment concerns a plasticizer comprising n-butyl isobutyl terephthalate.

A third embodiment concerns a method of making n-butyl isobutyl terephthalate comprising contacting n-butanol, isobutanol and dimethyl terephthalate in the presence of a catalyst.

Yet another embodiment concerns a method of making a mixture of terephthalate diesters comprising contacting a first alcohol, a second alcohol and dimethyl terephthalate in the presence of a catalyst, wherein the first alcohol and the second alcohol are different.

DETAILED DESCRIPTION

The present invention pertains to the preparation of n-butyl isobutyl terephthalate as well as a mixture of terephthalic acid diesters having a low melting point. The mixture includes 1) di-n-butyl terephthalate; 2) n-butyl isobutyl terephthalate; and 3) diisobutyl terephalate. Generally, the reaction forming the n-butyl isobutyl terephthalate and/or mixture of terephthalic acid diesters can be represented by the following equation:

To produce n-butyl isobutyl terephthalate and/or the terephthalic acid diester mixture, a batch or continuous reactor can be used to react n-butanol/isobutanol mixtures with dimethyl terephthalate (DMT) in the presence of a transesterification catalyst. For example, the reactor can be fitted with a simple distillation column and access ports for charging DMT, the alcohol mixture, and catalyst. In practice, the reactor is charged with DMT, varying mole-ratios of n-butanol/isobutanol, and a catalytic amount of a catalyst, such as tetraisopropoxy titanate (TIPT). Heating and stirring the mixture to reflux results in production of methanol via transesterification, which is selectively removed at the top of the distillation column. Conversion to the n-butanol/isobutanol ester mixture is essentially complete in six to eight hours. The crude product is then stripped of the excess unreacted alcohol mixture, treated with 2.5% NaOH to quench the titanate catalyst, washed with water and vacuum dried at reduced pressure. An activated carbon treatment can be employed to reduce color in the final product.

The catalyst used in the present method is a transesterification catalyst. Moreover, the catalyst may be a compound soluble in the reaction mixture, i.e., soluble in the alcohol and the terephthalic acid diester product. For example, the catalyst can be a titanium catalyst. An example of suitable titanium compounds include titanium tetraalkoxides having the formula $Ti(OR)_4$ wherein R is an alkyl group of 1 to 8 carbon atoms. An example being tetraisopropoxytitanate which is commonly abbreviated as TIPT. The catalyticallyeffective amount of the titanium compound generally is an amount which provides a titanium [Ti] concentration range of about 10 to 2000 parts per million by weight, 75-1000 parts per million by weight, or 100-200 parts per million by weight in the reaction mixture. Other suitable catalysts include titanium tetrabutoxide, tin tetraethoxide, dimethyltin aceate, tin oxide, butyl stanoic acid, dibutyltin oxide, and zirconium tetraisopropoxide.

The mixture can also be created by mixing the two pure diesters, adding the TIPT transesterification catalyst, and heating. Higher molecular weight alcohols converted to the dialkyl terephthalates that are considered waxes or solids at room temperature could also be converted to the mixed esters to give composite products that are lower melting.

The process can be conducted with a range of about 0.5:1.0 to about 4.0:1.0 mole ratio of n-butanol/isobutanol, or about 0.75:1.0 to about 3.0:1.0 mole ratio of n-butanol/isobutanol, or even about 1.0:1.0 to about 2.0:1.0 mole ratio of n-butanol/isobutanol.

The unreacted alcohol mixture can be readily recycled to the process. The process may be practiced in the continuous mode by adding the DMT to a suitable reactor in the molten form and the alcohol/TIPT mixture is fed by another pump to a stirred reactor equipped with a column such that the methanol of reaction can be removed and the unreacted higher alcohols returned to the reactor in the reflux. The effluent from this reactor can be passed to a chain of one or more finishing reactors wherein the conversion to the ester mixture with removal of methanol is continued. The product of this reaction can be further processed and refine by steps that are compatible with those listed for the batch example.

EXAMPLES

In the examples described below, the equipment used consisted of a one-liter base fitted with a heating mantel, magnetic stirrer bar, temperature sensor, and 10" Penn State-packed distillation column. The top of the column was fitted with a variable rate take-off head to allow selective removal of the methanol.

Each example was run under typical reaction conditions by conducting the reaction at reflux while removing methanol via the packed column at a take-off ratio of 1:4. At the completion of the reaction, the excess alcohol was then stripped from the base after replacing the fractionating column with a 3" Vigreux column and applying vacuum to a final pressure of 18 mm Hg. The crude product was treated with 2.5% aqueous NaOH to neutralize the TIPT catalyst and washed twice with deionized water. The material was then suction filtered through a glass fiber filter circle coated with Dicalite filter-aid. The product was subsequently dried at a final base temperature of ~120° C. at 1 mm Hg and held one hour. After cooling to 90° C., activated carbon (0.2 wt. %) was added and held at this temperature while stirring for one hour. The final product was isolate by filtration through a glass fiber filter coated with Dicalite filter-aid.

Example 1

The reaction was conducted in accordance with the chemical equation generally illustrated above on page 3 and was designed to produce a product derived from a 50:50 mole percent mixture of n-butanol and isobutanol.

The reactor system was charged with 436.9 g (2.25 mol, MW=194.19) of dimethyl terephthalate, 207.5 g (2.8 mol, MW=74.12) of n-butanol, 207.5 g (2.8 mol, MW=74.12) of isobutanol and 223 ppm (0.19 g) of tetraisopropoxy titanate (TIPT). The reaction progress is summarized in the Table 1 below:

TABLE 1

| Time | Reaction Time (hrs) | Base Temp C. | Take-off Temp C. | Take-off Vol. mL | Comments |
|---|---|---|---|---|---|
| 7:05 | — | 25 | 24 | 0 | |
| 8:00 | 0.0 | 119 | 98 | 0 | Start reaction time; set take-off at <66 C. |
| 8:30 | 0.5 | 111 | 65 | 5 | |
| 9:00 | 1.0 | 112 | 65 | 25 | |
| 9:30 | 1.5 | 115 | 66 | 45 | |
| 10:00 | 2.0 | 117 | 67 | 70 | |
| 10:30 | 2.5 | 119 | 67 | 85 | |
| 11:00 | 3.0 | 121 | 67 | 110 | |
| 11:30 | 3.5 | 125 | 66 | 130 | |
| 12:00 | 4.0 | 129 | 66 | 140 | |
| 12:30 | 4.5 | 127 | 70 | 144 | |
| 13:00 | 5.0 | 130 | 65 | 150 | |
| 13:30 | 5.5 | 138 | 66 | 160 | |
| 14:00 | 6.0 | 143 | 66 | 168 | |
| 14:30 | 6.5 | 147 | 68 | 170 | |
| 15:00 | 7.0 | 149 | 66 | 175 | Shutoff |

The product was stripped as summarized in Table 2 below:

TABLE 2

| Stripping Time | Strip Time (hrs) | Base Temp C. | Take-off Temp C. | Take-off Vol. ml | Comments | Vacuum mm Hg |
|---|---|---|---|---|---|---|
| 10:00 | 0.0 | 25 | 23 | 0 | | 16 |
| 11:00 | 1.0 | 113 | 35 | 90 | | 18 |
| 11:30 | 1.5 | 155 | 32 | 95 | | 18 |
| 12:00 | 2.0 | 154 | 28 | 98 | Shut off; Take-off Volatiles wt. = 77.4 g | 17 |

After neutralization, drying, carbon treatment and final filtration in accordance with the above-describe general work-up procedure, the isolated product weighed 547.7 g. The theoretical amount of product is 626.28 g for an 87.5% isolated yield.

Example 2

The reaction described in Example 1 was repeated to produce a product derived from a 75:25 mole percent mixture of n-butanol and isobutanol, respectively. The reactor system was charged with 233 g (1.2 mol, MW=194.19) of dimethyl terephthalate, 200.1 g (2.78 mol, MW=74.12) of n-butanol, 66.7 g (0.9 mol, MW=74.12) of isobutanol and 220 ppm (0.11 g) of TIPT. The reaction progress is summarized in the Table 3 below:

TABLE 3

| Time | Reaction Time (hrs) | Base Temp C. | Take-Off Temp C. | Take-Off Volume (ml) | Comments |
|---|---|---|---|---|---|
| 7:00 | — | 26 | 25 | 0 | Heating |
| 8:10 | 0.0 | 113 | 65 | 0 | Start reaction time and take-off at 20% <60 C. |
| 8:40 | 0.5 | 113 | 65 | 20 | |
| 9:40 | 1.5 | 119 | 65 | 55 | |

TABLE 3-continued

| Time | Reaction Time (hrs) | Base Temp C. | Take-Off Temp C. | Take-Off Volume (ml) | Comments |
|---|---|---|---|---|---|
| 10:10 | 2.0 | 123 | 66 | 70 | |
| 10:40 | 2.5 | 128 | 65 | 78 | |
| 11:10 | 3.0 | 131 | 66 | 88 | |
| 12:10 | 4.0 | 133 | 66 | 92 | |
| 13:10 | 5.0 | 134 | 66 | 93 | |
| 14:40 | 6.5 | 134 | 66 | 93 | |
| 15:40 | 7.5 | 134 | 66 | 93 | Shut-off; product as X-29455-162-01; take-off as 162-02 wt-70.1 g |

The product was stripped as summarized in Example 1 above and isolated as a clear liquid after neutralization, drying, carbon treatment and final filtration.

Example 3

The reaction described in Example 1 was repeated to produce a product derived from a 25:75 mole percent mixture of n-butanol and isobutanol, respectively. The reactor system was charged with 233 g (1.2 mol, MW=194.19) of dimethyl terephthalate, 66.7 g (0.9 mol, MW=74.12) of n-butanol, 200.1 g (2.7 mol, MW=74.12) of isobutanol and 280 ppm (0.14 g) of TIPT. The reaction progress is summarized in the Table 4 below:

TABLE 4

| Time | Reaction Time (hrs) | Base Temp C. | Take-Off Temp C. | Take-Off Vol (ml) | Comments |
|---|---|---|---|---|---|
| 8:00 | — | 102 | 22 | 0 | |
| 8:30 | 0.0 | 116 | 93 | 0 | Start reaction time; turn on take-off @ <66 C. @ 20% |
| 9:00 | 0.5 | 109 | 65 | 0 | |
| 9:30 | 1.0 | 106 | 64 | 0 | Lifter not working; shut-off and replaced |
| 10:15 | | 84 | 25 | 0 | Began heating |
| 10:55 | 1.0 | 106 | 64 | 0 | Start take-off at 20% |
| 11:55 | 2.0 | 112 | 64 | 12 | |
| 12:55 | 3.0 | 116 | 66 | 28 | |
| 13:25 | 3.5 | 116 | 66 | 34 | |
| 13:55 | 4.0 | 116 | 66 | 42 | |
| 14:25 | 4.5 | 117 | 65 | 50 | Base heater output @ 53 |
| 14:55 | 5.0 | 118 | 65 | 57 | |
| 15:25 | 5.5 | 119 | 65 | 68 | Shutoff |
| 8:25 | 5.5 | 120 | 64 | 68 | Start take-off at 20% |
| 9:25 | 6.5 | 125 | 65 | 78 | |
| 9:55 | 7.0 | 126 | 66 | 82 | |
| 10:25 | 7.5 | 128 | 66 | 85 | |
| 11:25 | 8.5 | 130 | 66 | 88 | |
| 12:25 | 9.5 | 132 | 66 | 92 | |
| 12:55 | 10.0 | 130 | 67 | 92 | |
| 13:25 | 10.5 | 130 | 66 | 93 | |
| 14:25 | 11.5 | 130 | 66 | 93 | Shutoff |

The product was stripped as summarized in Example 1 above and isolated as a partially solid material after neutralization, drying, carbon treatment and final filtration. Since the goal was to develop lower freezing products, no further work was done with this material.

Each sample was analyzed by capillary gas chromatography (uncorrected area percent values reported). The results are summarized in Table 5 below:

TABLE 5

| Sample ID | Methyl Isobutyl Terephthalate | Methyl n-Butyl Terephthalate | DIBT | n-Butyl-Isobutyl Terephthalate | DBT |
|---|---|---|---|---|---|
| 158-01 | 3.48% | 3.73% | 26.33% | 39.45% | 26.85% |
| 163-01 | 0.47% | 1.53% | 10.47% | 38.20% | 49.18% |
| 164-01 | 0.99% | 0.36% | 48.44% | 39.04% | 10.58% |

Freezing Point Study

Figure 1:
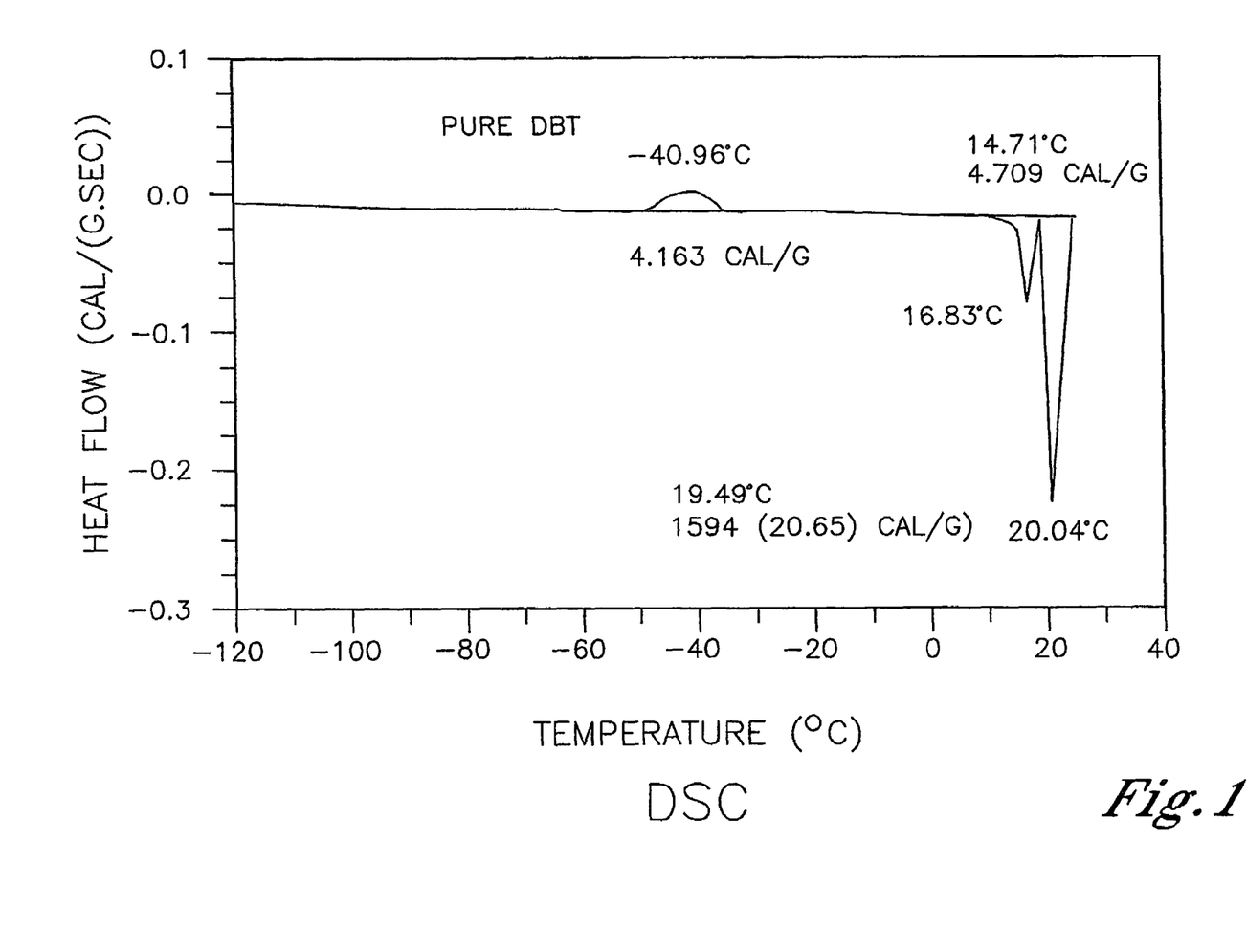
FIG. 1 shows a DSC melting point study of pure DBT.
Figure 2A:
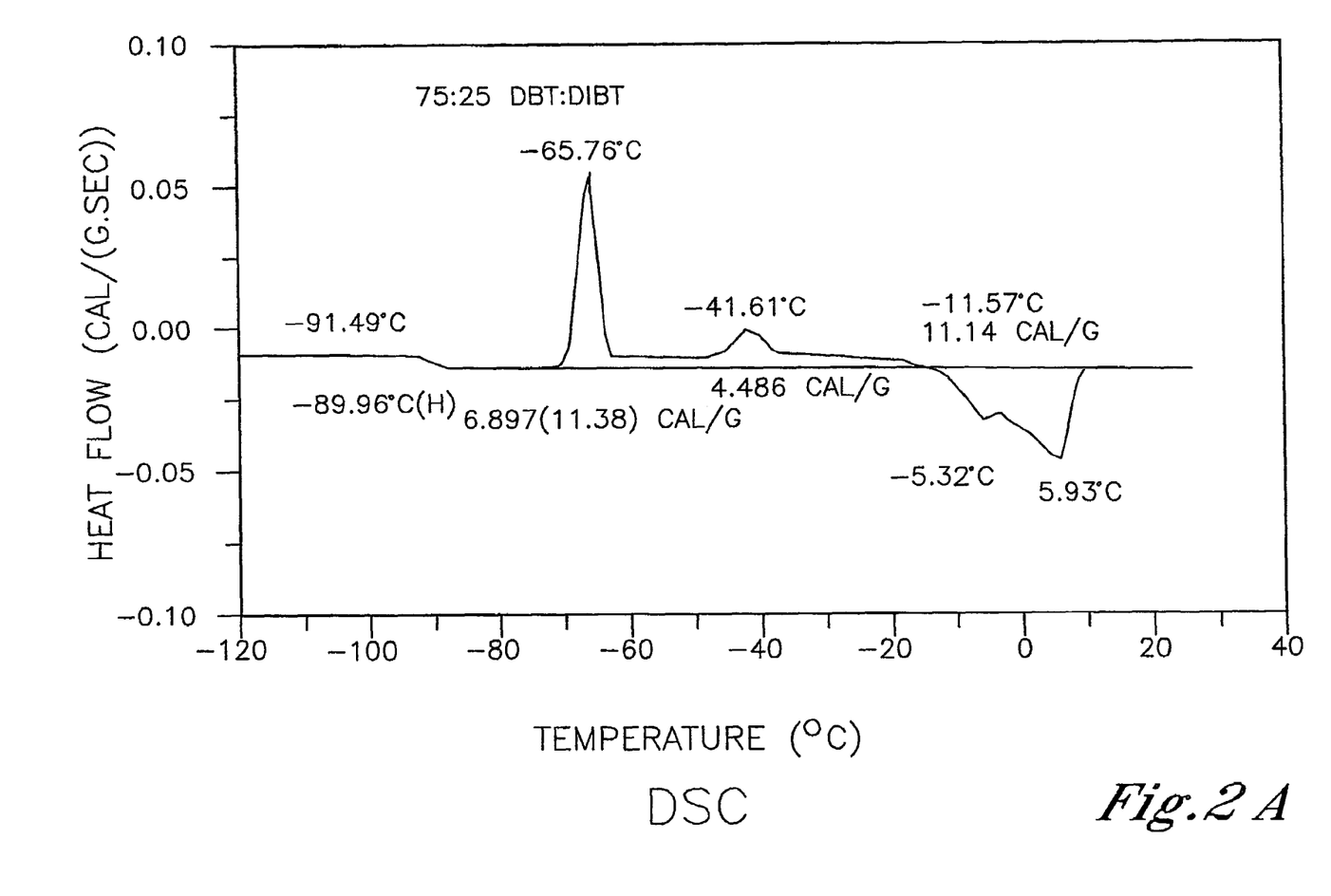
FIGS. 2a and 2b show a DSC melting point study for 75:25 and 50:50 DBT:DiBT, respectively.
Figure 2B:
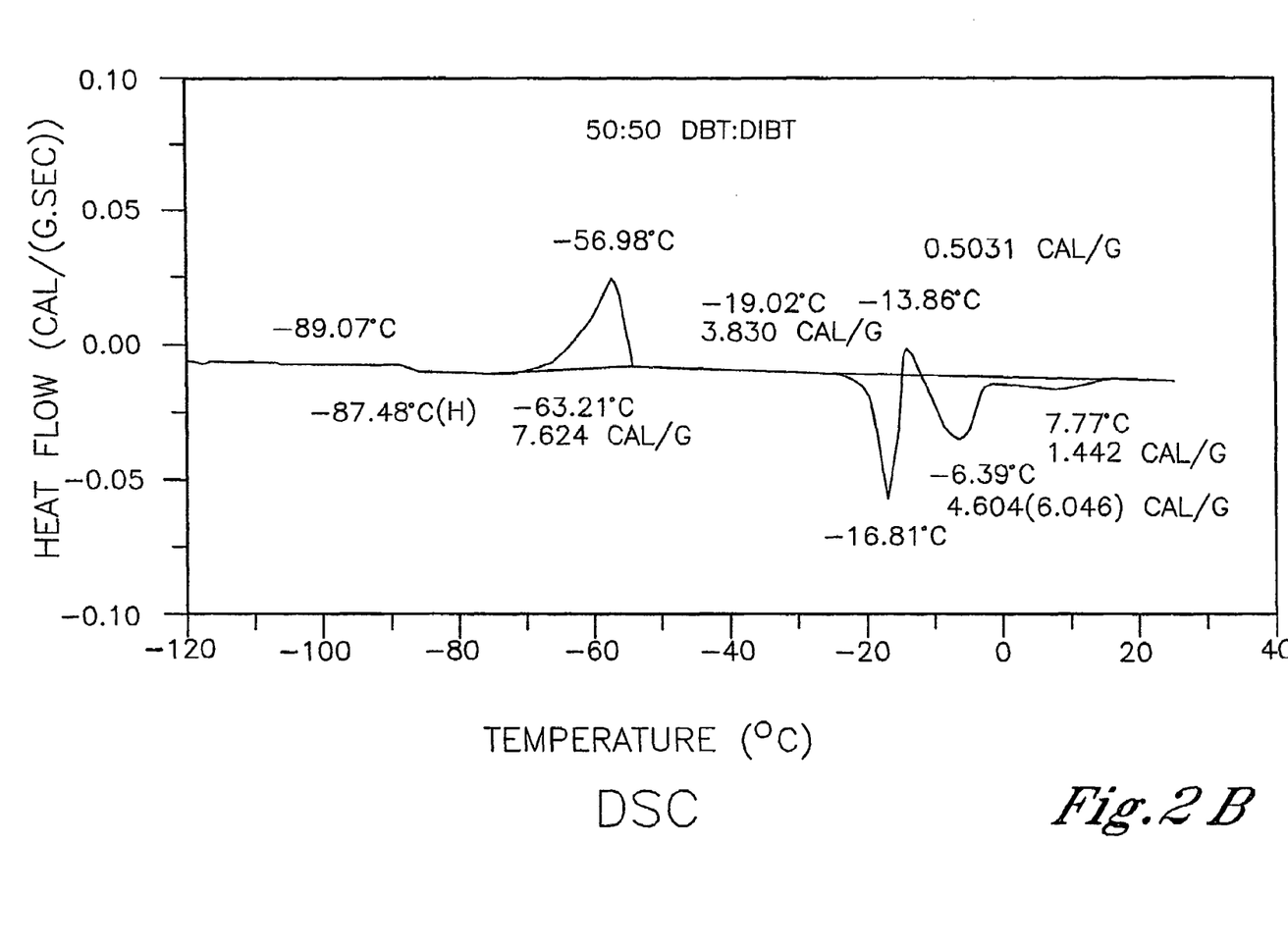
Figure 3A:
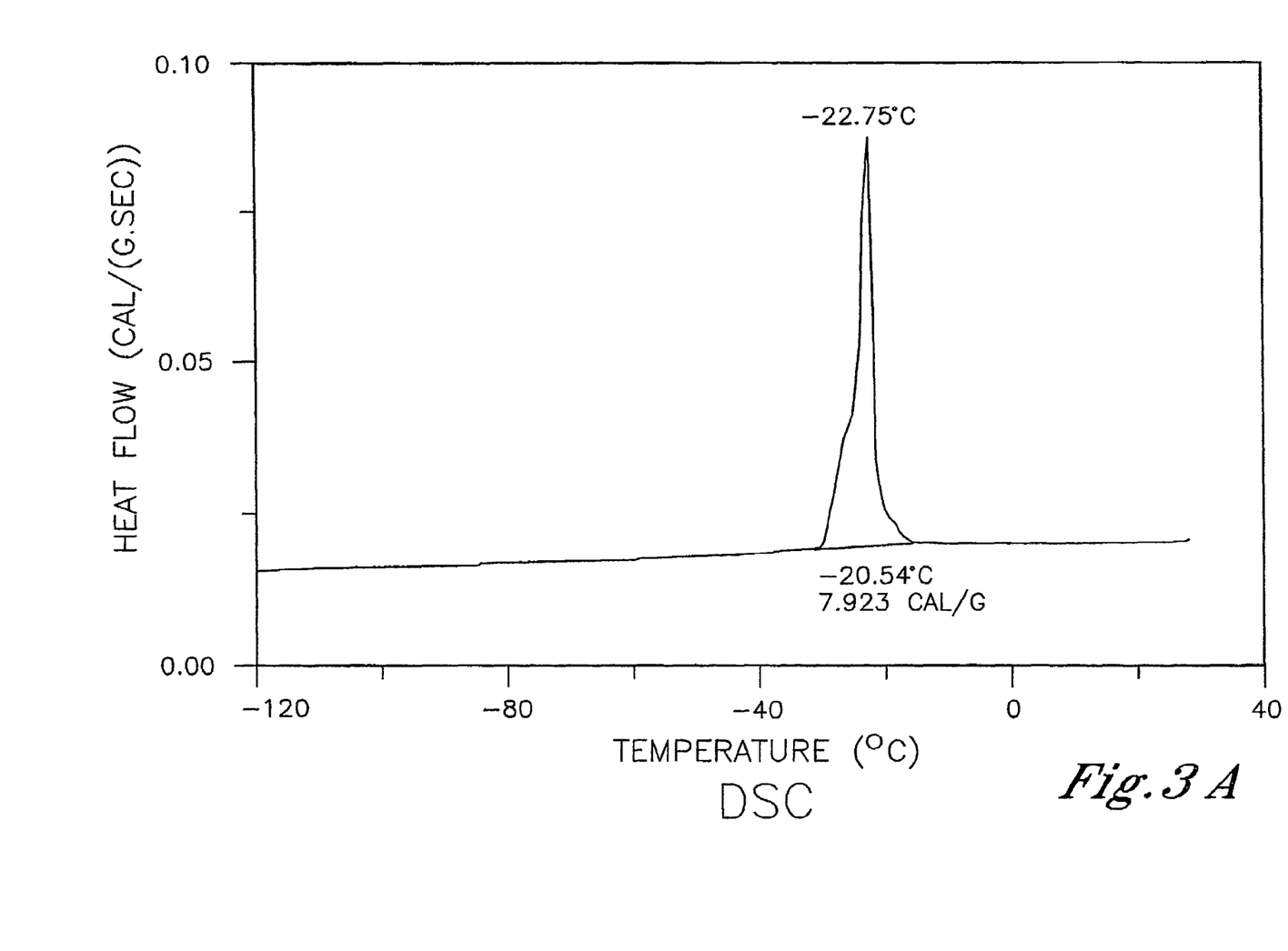
FIGS. 3a and 3b show a DSC freezing point study for 75:25 and 50:50 DBT:DiBT, respectively.
Figure 3B:
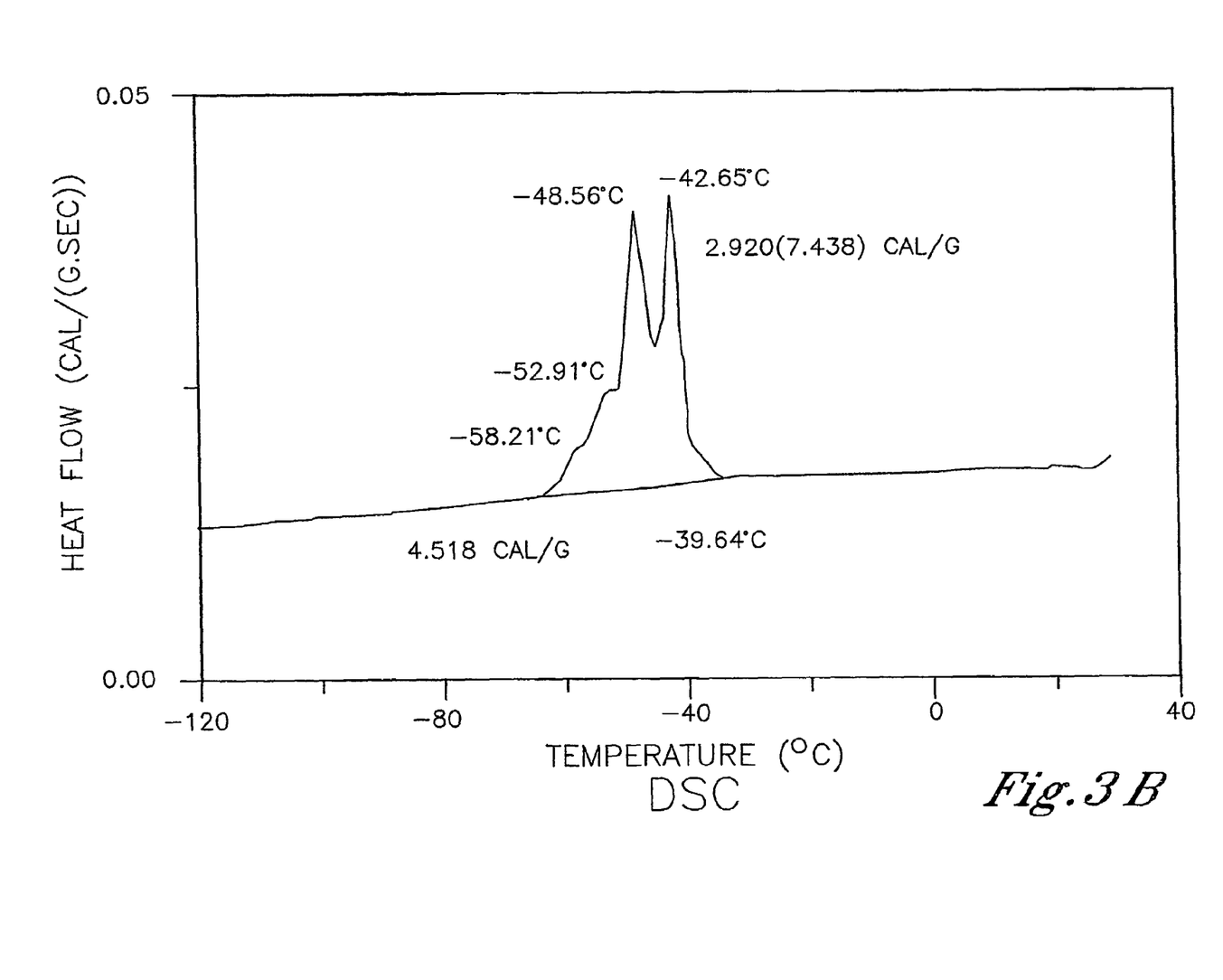
Figure 4:
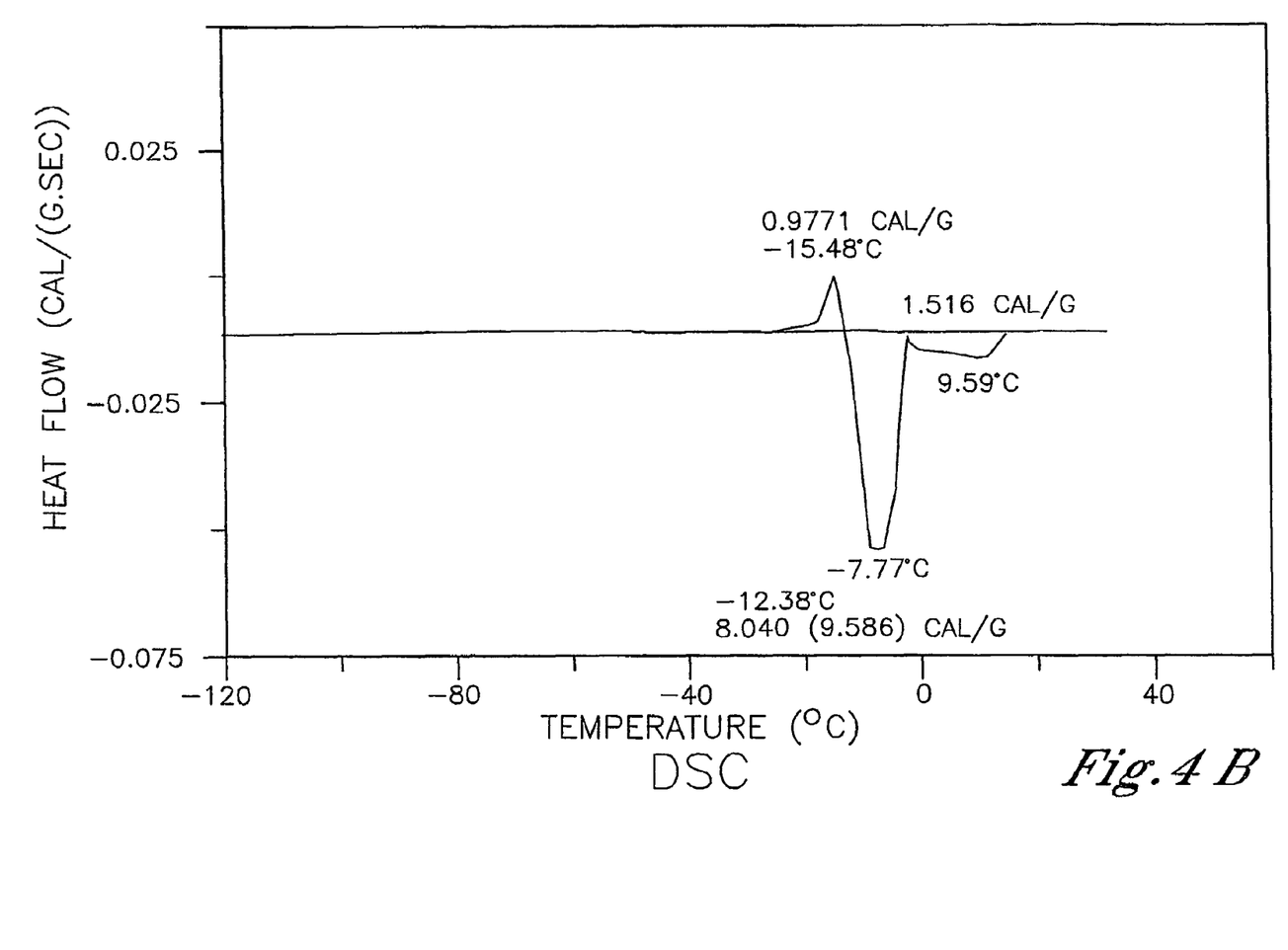
FIGS. 4a and 4b show a second DSC melting point study for the 75:25 and 50:50 DBT:DiBT, respectively.
Figure 4A:
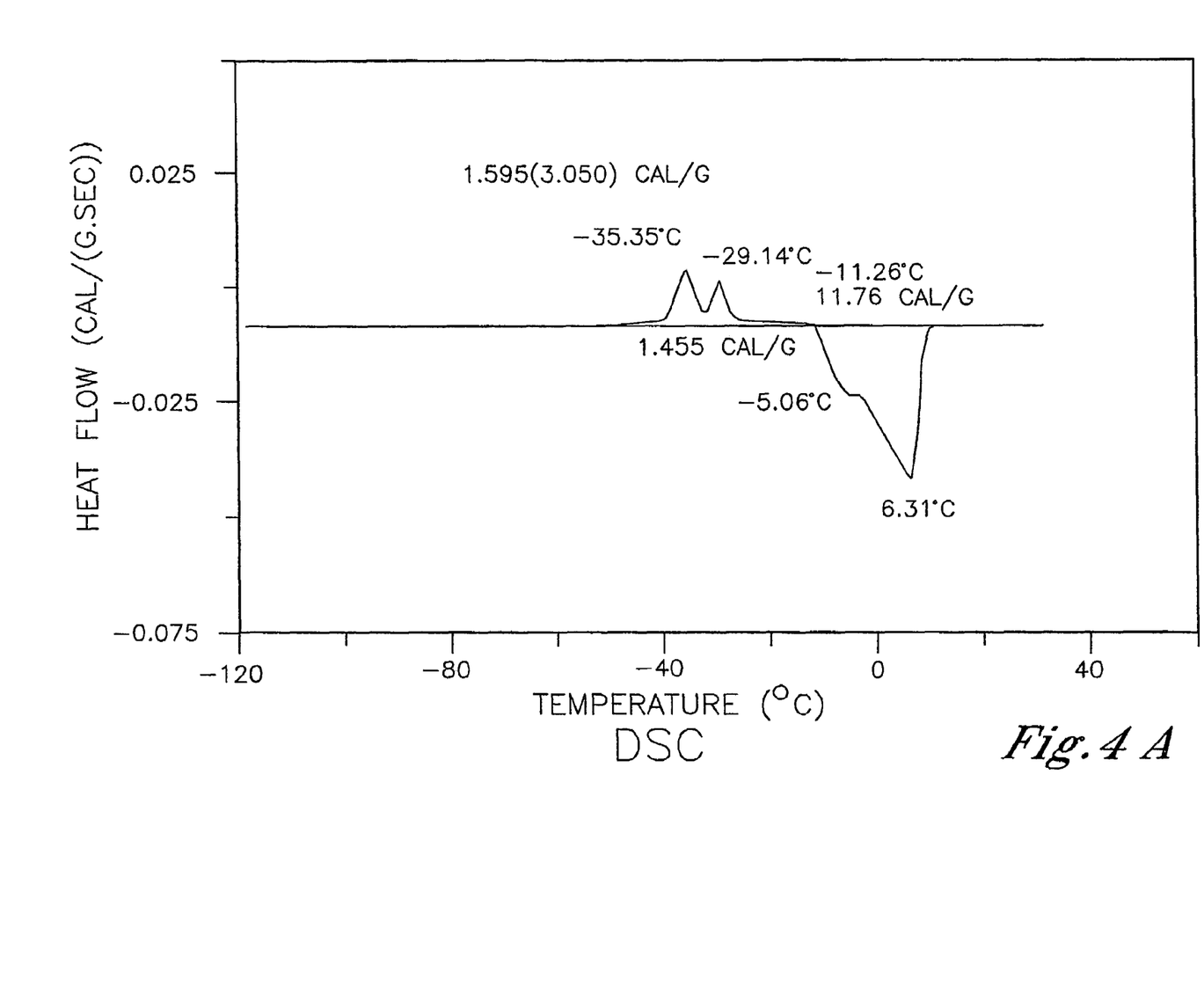

Two of the above materials (158-01, 163-01) along with pure DBT were submitted for a DSC point study. This study incorporated heat-cool-heat cycles in an hermetically sealed stainless steel pan. The scan rate was 2° C./min. in helium. FIG. 1 is the warm-up cycle for pure DBT.

The results show a complex freezing point behavior. For the 75:25 DBT/DIBT mixture:

1. On the first warm-up, there are two crystallization events at −66 and −42 followed by a minor melting event at −5 and a major one at 6.

2. On the second warm-up, it goes through two crystallization events at −35 and −29 followed by a minor melting event at −5 and a major one at 6.

3. The freezing point peaked at around −42 (super cooled).

For the 50:50 mixture:

1. The freezing point peaked at around −22° C. (super cooled).

2. On the first warm-up it goes through two low-temperature events: crystallized at −56 and melted at −17 followed with another melting at −6 and a final melting event at 8.

3. On the second warm-up, it goes through one crystallization event at −15 and one melt event at −8 followed with a minor melting event at 10.

Of the two, the 50:50 looks the best in that there is a smaller melting event at the warmer region (minor at 8-10 vs. major at 6 for 75:25). On the other hand, the 75:25 seems to super cool to a lower temperature than the 50:50 (−42 vs. −22).

Figure 5:
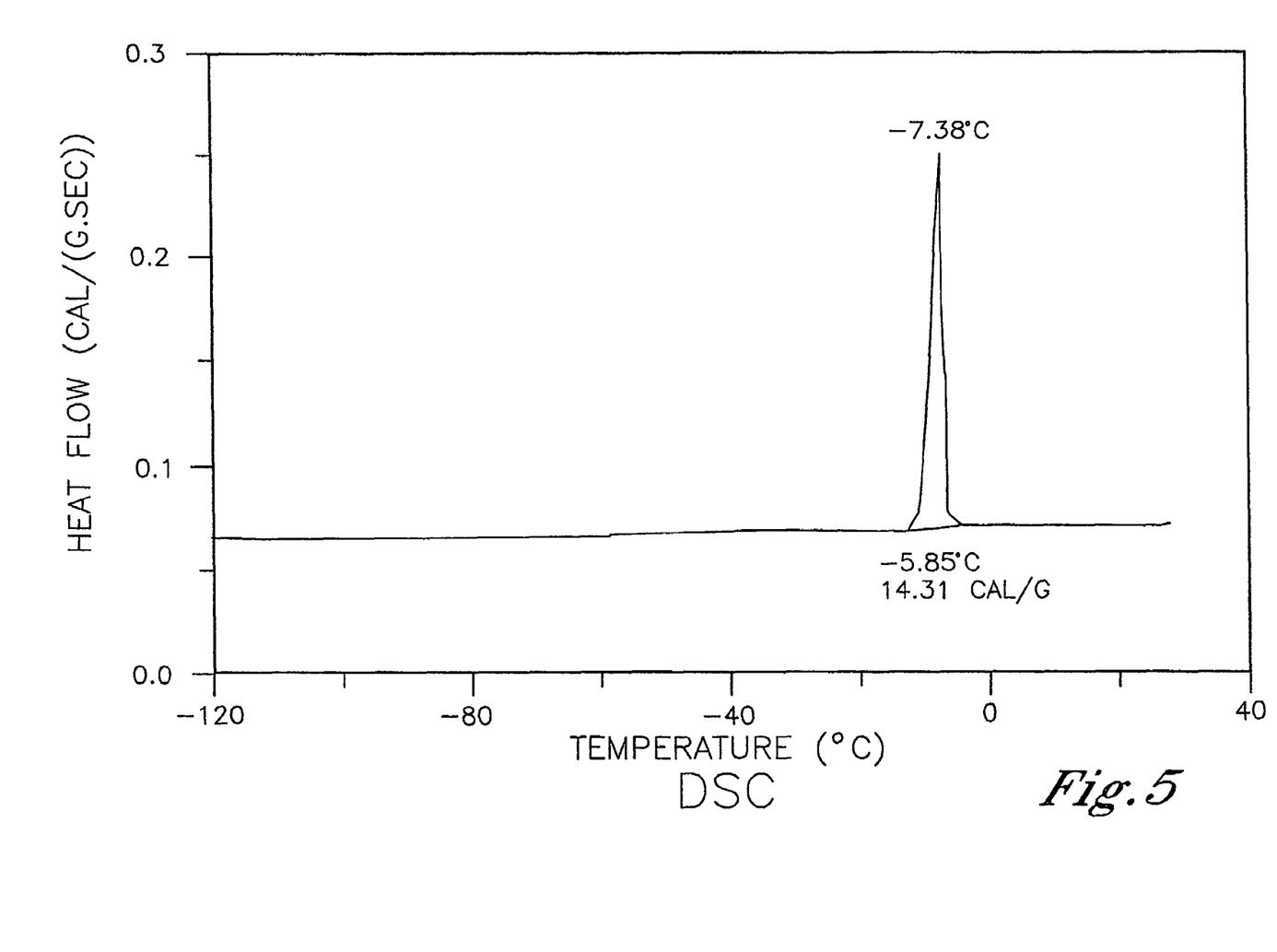
FIG. 5 shows a DSC freezing point study of pure DBT.

Note that the DBT super cooled to −7 before freezing, as shown in FIG. 5:

The invention has been described in detail with particular reference to preferred embodiments thereof, but it will be understood that variations and modifications can be effected within the spirit and scope of the invention.

We claim:

1. A composition comprising n-butyl isobutyl terephthalate.

2. The composition according to claim 1, further comprising di-n-butyl terephthalate and diisobutyl terephthalate.

3. A plasticizer comprising n-butyl isobutyl terephthalate.

4. The plasticizer according to claim 3, further comprising di-n-butyl terephthalate and diisobutyl terephthalate.

5. A method of making n-butyl isobutyl terephthalate comprising:

contacting n-butanol, isobutanol and dimethyl terephthalate in the presence of a catalyst.

6. The method according to claim 5, wherein said catalyst is a transesterification catalyst.

7. The method according to claim 6, wherein said catalyst is tetraisopropoxy titanate.

8. The method according to claim 5, wherein the n-butanol and isobutanol are present in an amount of from about 0.5:1.0 to about 4.0:1.0 mole ratio of n-butanol/isobutanol.

9. The method according to claim 8, wherein the n-butanol and isobutanol are present in an amount of from about 0.75:1.0 to about 3:1.0 mole ratio of n-butanol/isobutanol.

10. The method according to claim 9, wherein the n-butanol and isobutanol are present in an amount of from about 1.0:1.0 to about 2.0:1.0 mole ratio of n-butanol/isobutanol.

* * * * *